US006963396B2

(12) United States Patent
Kimberlin

(10) Patent No.: US 6,963,396 B2
(45) Date of Patent: Nov. 8, 2005

(54) LIGHT HOLE INSPECTION SYSTEM FOR ENGINE COMPONENT

(75) Inventor: Dwight Evans Kimberlin, Cincinnati, OH (US)

(73) Assignee: Meyer Tool, Inc., Cincinnati, OH (US)

( * ) Notice: Subject to any disclaimer, the term of this patent is extended or adjusted under 35 U.S.C. 154(b) by 151 days.

(21) Appl. No.: 10/608,248

(22) Filed: Jun. 27, 2003

(65) Prior Publication Data

US 2004/0263837 A1 Dec. 30, 2004

(51) Int. Cl.$^{7}$ .................................................. G01N 21/01
(52) U.S. Cl. .................................. 356/237.6; 356/241.1
(58) Field of Search ........................... 356/237.1–237.6, 356/241.1, 241.3–241.6; 382/8, 62, 54

(56) References Cited

U.S. PATENT DOCUMENTS 4,145,714 A * 3/1979 MacDonald et al. ........ 348/131
4,560,273 A * 12/1985 Ando et al. .............. 356/237.6
4,596,037 A * 6/1986 Bouchard et al. ........... 382/141
4,667,231 A * 5/1987 Pryor ......................... 348/128
4,712,916 A * 12/1987 Gunn ...................... 356/241.1
4,865,448 A * 9/1989 Akutsu et al. ........... 356/241.1
5,197,105 A * 3/1993 Uemura et al. ............. 382/147
5,610,710 A * 3/1997 Canfield et al. ......... 356/237.6

* cited by examiner

*Primary Examiner*—Michael P. Stafira
(74) *Attorney, Agent, or Firm*—Wood, Herrron & Evans, L.L.P.

(57) ABSTRACT

A hole inspection system having a light source emitting light over its length and a multi-axes machine having a camera mounted thereon. After the light source is inserted into a cavity intersecting the complex holes, a control commands the multi-axes machine to move the camera to an inspection position associated with one of the complex holes. The control processes substantially only light intensity values received from the camera that represent light shining through the one of the complex holes. Next, a maximum intensity value of light received by the camera from the one of the complex holes is determined. The maximum intensity value is compared to a threshold value, and error data is created that identifies the one of the complex holes in response to the maximum intensity value being less than the threshold value.

22 Claims, 5 Drawing Sheets

LIGHT HOLE INSPECTION SYSTEM FOR ENGINE COMPONENT

FIELD OF THE INVENTION

The present invention relates to manufacturing gas turbine engine components and, more particularly, to inspecting complex cooling holes through a surface of a gas turbine engine component.

BACKGROUND OF THE INVENTION

During operation, gas turbine engines, whether used for flight or stationary power generation, develop extremely high temperature and high velocity gases in a combustor portion of the engine. These gases are ducted on blades of a turbine rotor to cause rotation of the rotor and are redirected by the stator vanes onto additional rotor blades to produce more work. Because of the high heat of the gases, it is desirable to cool the blades and vanes to prevent damage and, to extend the useful life of, these engine components. It is known in the art that turbine components can be cooled by film cooling that is provided by a plurality of cooling holes. These holes are small have a complex shape; and often, there is a large number of cooling holes in the surface to be cooled.

After the cooling holes have been manufactured, it is necessary to inspect each of the holes to determine whether it exists and is properly formed as a complex hole. One method of inspection is a manual method in which an inspector is provided with a drawing of the desired hole pattern and a pin. The inspector first confirms that a hole exists at each location identified by the pattern; and then, the inspector inserts the pin through each of the holes to determine whether the hole is properly drilled as a through-hole. As can be appreciated, such an inspection process is highly repetitive, tedious and stressful for the inspector and, in addition, is expensive and inefficient for the manufacturer of the turbine component. Other inspection processes are known that are somewhat less tedious, but all of the processes known to applicant are based on human visual inspection.

Thus, there is a need for an inspection apparatus and process that can automatically inspect complex cooling holes in gas turbine components faster, more precisely and less expensively than known devices and methods.

SUMMARY OF THE INVENTION

The present invention provides an inspection apparatus and process that automatically inspects for the presence of through-holes in a gas turbine component. The inspection apparatus and method of the present invention is faster, more error-free and less expensive than known tactile and visual inspection methods. Thus, the inspection apparatus and method of the present invention is especially useful for inspecting a presence and quality of a large number of complex cooling holes in gas turbine component.

According to the principles of the present invention and in accordance with the described embodiments, the invention provides a hole inspection system for inspecting complex holes. The hole inspection system has a light source emitting light over its length and a multi-axes machine having a camera mounted thereon. After the light source is inserted into a cavity intersecting the complex holes, a control commands the multi-axes machine to move the camera to inspection positions associated with each of the complex holes. The control processes substantially only light intensity values received from the camera that represent light shining through a respective complex hole.

In another embodiment, the invention provides a method of inspecting the complex holes by first illuminating an internal cavity intersecting the complex holes with a light source emitting light over its length. Then, a camera is moved to an inspection position associated with one of the complex holes; and thereafter, a maximum intensity value of light received by the camera from the one of the complex holes is determined. The maximum intensity value is compared to a threshold value, and error data is created that identifies the one of the complex holes in response to the maximum intensity value being less than the threshold value. The above process is repeated for each of the complex holes being inspected.

These and other objects and advantages of the present invention will become more readily apparent during the following detailed description taken in conjunction with the drawings herein.

DETAILED DESCRIPTION OF THE INVENTION

Figure 1:
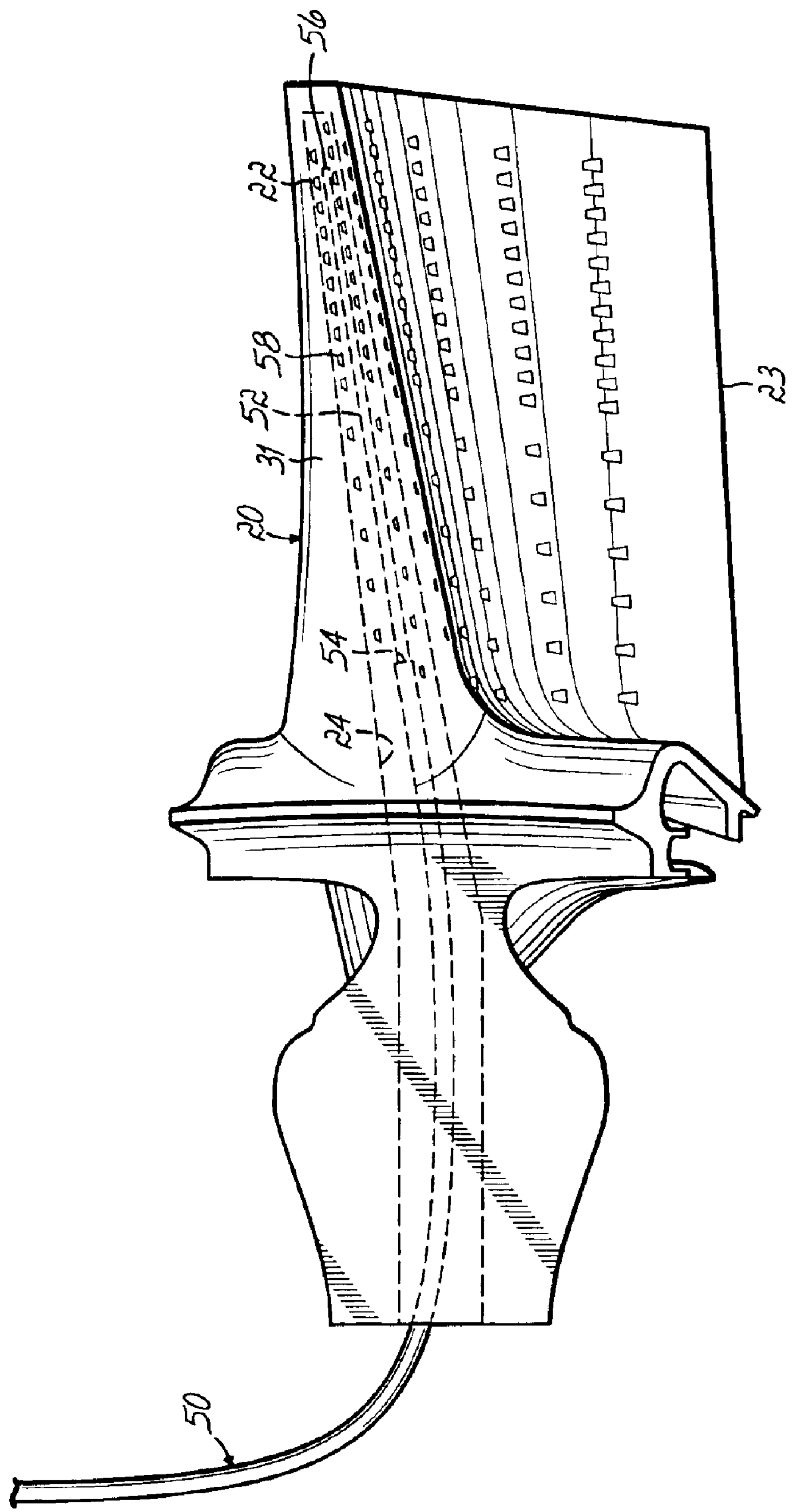
FIG. 1 is a partial perspective view of an example of a known turbine component that utilizes rows of cooling holes similar to the complex hole of FIG. 1.

Referring to FIG. 1, a turbine component 20 is cooled by venting cooling air through a plurality of cooling holes 22. The cooling holes 22 are typically formed along a line substantially parallel to, and a selected distance from, a trailing edge 23 of the component to provide a film of cooling air over an outer surface 31 of the component 20 when the cooling holes 22 discharge air during engine operation. The cooling air is supplied to the cooling holes 22 by one or more internal cavities or passages 24 that are supplied cooling air from a source (not shown) in a known manner. This air cools internal surfaces of the component by convection and cools the components outer surfaces by film cooling.

Figure 2:
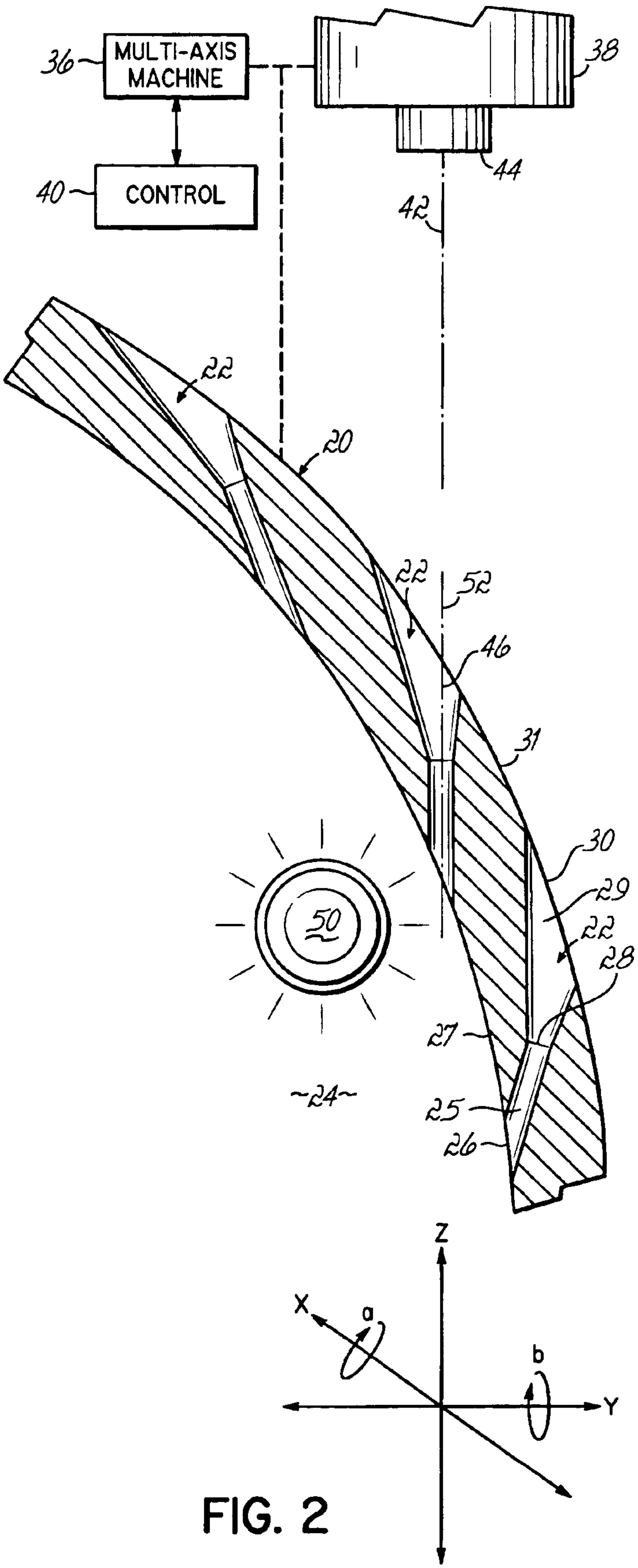
FIG. 2 is a cross-sectional side view of a light inspection system for inspecting a complex hole formed in a part in accordance with the principles of the present invention.

Referring to FIG. 2, to facilitate the distribution of the cooling air substantially completely over the surfaces of the component 20, the upstream end of each cooling hole 22 has a generally cylindrical, inlet portion 25 that extends from an inlet orifice 26 on an inner surface 27 of the cavity 24. At a location 28, the cooling hole 22 then flares or diverges to provide a downstream discharge or diffuser portion 29 that extends from the interior location 28 to a discharge outlet orifice 30 on an exterior surface 31 of the component 20. The diffuser 29 is shaped to reduce the velocity of the cooling airstreams being discharged from the cooling holes 22. The lower velocity cooling airstreams are more inclined to cling to the surface 31 for improved cooling. As will be appreciated, the geometry of any particular hole can vary from hole to hole and from part to part. The complex cooling holes 22 are drilled using known EDM and/or laser drilling processes.

It is important that all of the cooling holes exit as through-holes for proper and uniform cooling; however, casting variances may result in a cooling hole being drilled as a blind hole. Therefore, it is necessary that each cooling hole be inspected; and as previously discussed, known processes are largely manual and rely on visual inspection by an inspector.

With the present invention, as shown in FIG. 2, the turbine component 20 is mounted on a multi-axes inspection machine 36, for example, a machine having six axes of motion. The inspection machine 36 often has a configuration that is substantially the same as the multi-axes machine used to drill the complex cooling holes 22. As described herein, the invention is practiced using only five of the six axes of the machine. A camera 38 is mounted in, or in place of, a spindle of the inspection machine 36. The inspection machine 36 is connected to a programmable control 40 with servo-controlled drives that are operable to provide relative motion between the machine 36 and the camera 38 along mutually perpendicular X, Y, and Z axes of linear motion. Further, an A-axis rotates the component 20 about an axis of rotation coincident with the X-axis, and a B-axis rotates the turbine component 20 about an axis of rotation coincident with the Y-axis. Thus, the A and B rotary axes permit a centerline 42 of a camera lens 44 to be oriented at any angle with respect to the component exterior surface 31. Further, the control 36 is operable to move the camera centerline 42 to desired positions and orientations, so that, for example, the camera centerline 42 can be substantially collinearly aligned with a centerline 46 of each of the complex cooling holes 22. The inspection machine 36 often has a C-axis that can rotate the component 20 about an axis of rotation coincident with the Z-axis, however, the present invention can be practiced without requiring C-axis motion.

Figure 3:
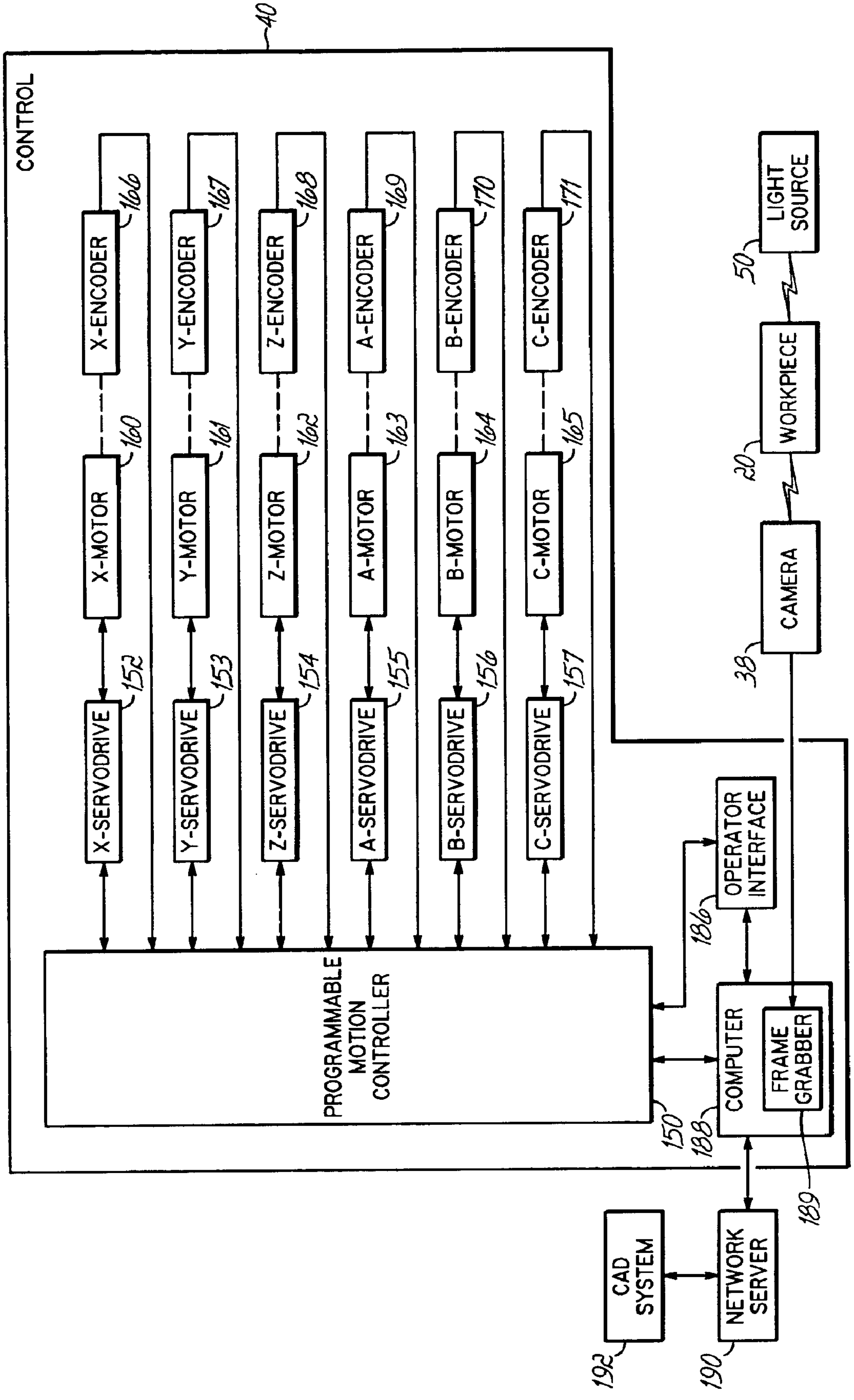
FIG. 3 is a schematic block diagram of a control for operating a multi-axes machine of the type used to inspect the complex hole of FIG. 1.

Referring to FIG. 3, the control 40 includes a programmable motion controller 150 that controls relative motion between the camera 44 and the turbine component 20 in a known manner. The motion controller 150 provides command signals to respective X, Y, Z, A, B, C servo drives 152–157, respectively. The servo drives 152–157 provide output signals commanding the operation of respective X, Y, Z, A, B, C motors 160–165, respectively. X, Y, Z, A, B, C encoders 166–171 are mechanically coupled to respective motors 160–165 and provide respective feedback signals to the motion controller 150.

The control 40 further includes an operator interface 186 that provides various user operable input devices, for example, pushbuttons, switches, etc., as well as various sensory perceptible output devices, for example, lights, a visual display such as an LCD screen, etc. The operator interface 186 permits the operator to manually operate the various servodrives. Also part of the control 40 is a computer 188, which is an industrialized PC that provides a communications interface between a network server 190 and the programmable motion controller 150 as well as the operator interface 186.

A CAD system 192 is also connected to the network server 190 and is operable to provide input data to the control 40. The CAD system 192 includes a digital model of the turbine component illustrated in FIG. 1. Within that model, the position and orientation of respective cooling hole centerlines 46 are defined with respect to X, Y, Z, A, B coordinates. In a premanufacturing process, the position and orientation of the centerlines of the cooling holes to be inspected are extracted from the model using the CAD system 192 and made available to the network server 190 as a set of input data. The operator uses the operator interface 186 to retrieve, via the network server 190, a set of input data from the CAD system 192 that corresponds to the turbine component 20 to be inspected; and that input data is stored in the computer 188.

It should be noted that the input data representing cooling hole centerline locations that was used to drill the complex cooling holes 22 can also be used in the hole inspection process. Therefore, if that input data remains stored in the computer 188, it can be used by the computer 188 to execute the hole inspection process without having to retrieve it from the CAD system 192.

The input data was created in a program language and data format that is compatible with the CAD system 192. However, the input data is to be utilized by the programmable motion controller 150 that has its own program language and data format. The computer 188 is operative to translate the input data from the program language and data formats of the CAD system 192 to a program language and data format that are usable by the programmable motion controller 150.

The programmable motion controller 150 has two major functions. First, it must modify the input data that was created with respect to a coordinate system in the CAD system 192 to a coordinate system that is specific to the inspection machine 36 being used. As will be appreciated, the physical structure of inspection machines varies with different models and manufacturers. For example, the configuration of machine slides representing different axes of motion vary; the length of travel of the axes of motion vary; the alignment or home positions for the axes of motion vary, etc. While all of the different machine configurations are capable of inspecting the turbine component 20, the different physical configurations require respectively different input data. Therefore, the first function of the motion controller 150 is to offset and/or reorient the input data from the computer 188 to input data that is specific to the inspection machine 36 on which the turbine component 20 is to be inspected. In addition, in a known manner, a setup procedure is executed by the operator during which the camera is aligned with a fixture holding the turbine component; and in that process, the motion controller 150 is provided further data that precisely identifies the location of the turbine component 20 with respect to the machine coordinate system. Thus, with this system architecture, a common set of part data can be used with inspection machines having a wide range of different configurations.

Second, once a hole inspection cycle of operation is initiated, the motion controller 150 is operable to create a path of relative motion between the camera 44 and the turbine component 20. A path of motion is defined by path segments, the endpoints of which are defined by coordinate values in the X, Y, Z, A, B axes. Thus, the endpoints collectively represent a locus of points generally defining the desired path of relative motion between the camera 44 and the turbine component 20. The motion controller 150 linearly interpolates camera motion along a path segment between the endpoints.

The cooling hole inspection process requires that a light source 50 be placed in a cavity 24 (FIG. 1) of the turbine component 20. Further, the light source should emit light or illumination over a length 52 extending from a point 54 to a distal end 56 of the light source 50. The point 54 is chosen so that the light emitting length 52 allows sufficient light to shine through the complex cooling holes 22, so that it can be received and properly processed by the camera 44. It should be noted that the cavity 24 often curves or bends within the component 20 and may be J-shaped to form two parallel passages. Further, there are often holes in sidewalls of the parallel passages, which interconnect the passages.

In some applications, the light emitting length 52 be able to extend over the full length of a curved passage, however, in such applications, wear on the light emitting length 52 is substantial; and in those applications, the useful life of the light source 50 is short. In other applications, the light emitting length 52 is limited to a substantially linear portion of the cavity 24, but the light emitting length is bright enough to shine through the holes interconnecting the passages and then out through the holes 22. Thus, the best light emitting length is often experimentally determined for different components 20.

The light source 50 must be small enough to fit into the cavity 24, and in one embodiment, is a fiber optic cable. There are several methods of creating a bar-like or longitudinal length of light 52 using a standard fiber optic cable that provides a point source of light of, for example, 150 watts. First, the sheath of the fiber optic cable is stripped a desired distance, for example, a distance that is greater than the desired light emitting length 52. The exposed optic fibers are fanned out evenly on a cutting surface over an angle of about 45 degrees and taped in place. Next, leaving about 10 fibers at full length, the remaining fibers are cut along a straight line that is angled about 45 degrees with respect to the centerline of the fiber optic cable. The result is a fan of fibers of different lengths with the shortest fibers having ends located at about at the point 54 and being about one-half the length of the longest fibers. In another embodiment the fibers are cut along a curved line having a chord extending between the ends of the longest and shortest fibers.

The fibers are then removed from the cutting surface formed back into a cylindrical cable, The fibers are moistened, so that they stay together; and clear heatshink tubing is shrunk over the fibers and stretched, so that all of the fibers are contained within the tubing. Then, an opaque or black heatshink tubing is shrunk over the portion of the fiber bundle that extends from a location over the fiber optic cable sheath to a location represented by the point 54, which is immediately adjacent ends of the shortest fibers.

Figure 4:
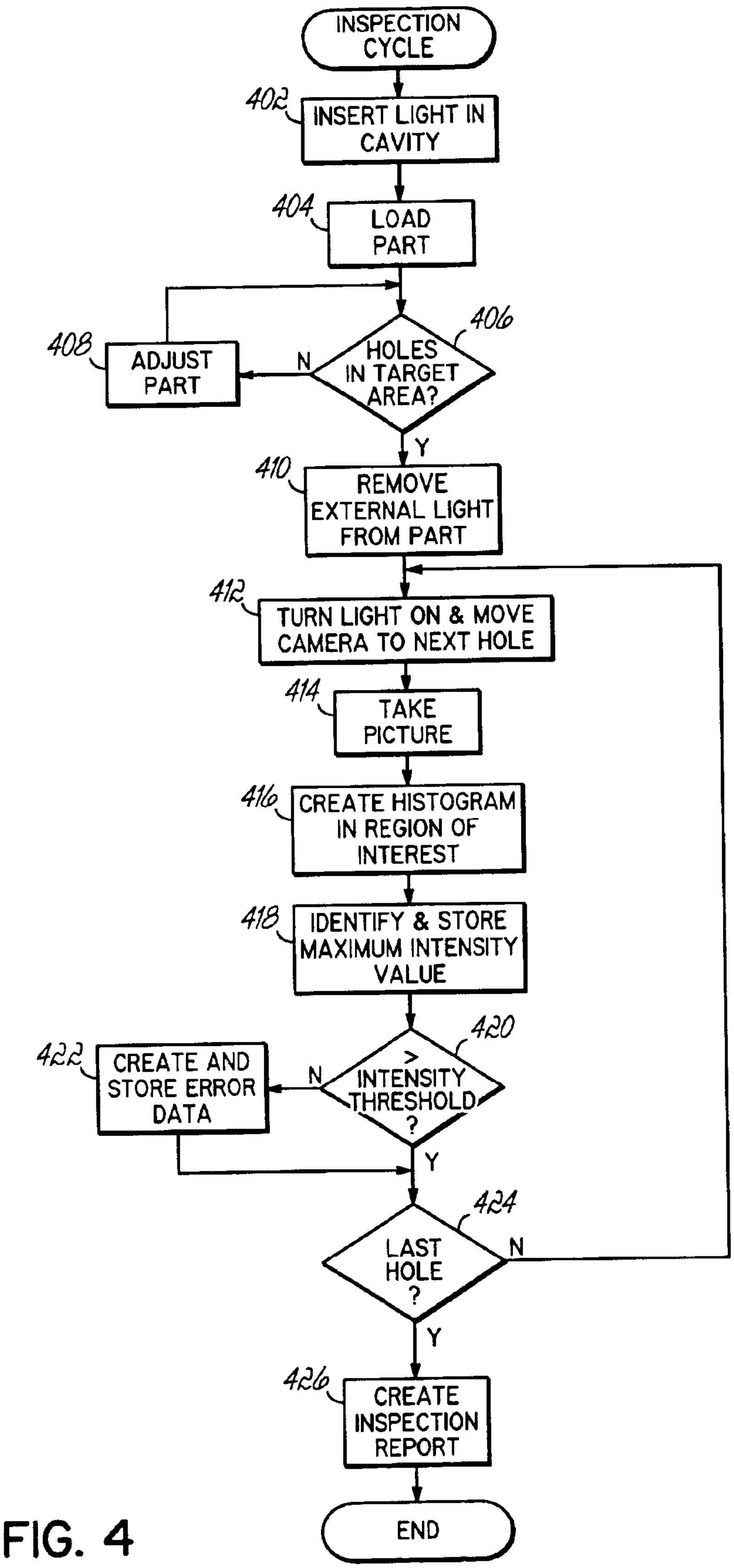
FIG. 4 is a flowchart of an inspection cycle using the light inspection system of FIG. 1.

Referring to FIG. 4, to initiate an inspection cycle, at 402, the light source 50 is inserted into the cavity 24 of the component 20. Some components have two cavities; and in those applications, a light source 50 would be inserted in each of the cavities. Next, at 404, the component 20 is loaded in the inspection machine 36. The operator then, at 406, determines whether the holes 22 of the component 50 are within the target area of the camera. To make this determination, the operator initiates, with the control 40, a positioning cycle during which the control 40 commands the machine 36 to move the camera 38 over each pole to be inspected. In that process, the motion controller 150 provides output signals to various servo drives 152–157 that, in turn, command respective motors 160–165 to operate in a coordinated manner to move the turbine component 20 and camera 38 relative to each other such that the camera centerline 42 is substantially colinear with a cooling hole centerline 52 as shown in FIG. 2. If the component 20 is not properly located on the machine 36, the operator will observe a misalignment between the camera centerline 42 and the cooling hole centerlines 52.

Next, in the inspection cycle of FIG. 4, at 410, external light is removed from the part. This is accomplished by turning off localized worklights and further, surrounding the machine 36 with an opaque cover or shroud to block ambient light from the camera 38. Thereafter, at 412, the operator turns on the light source 50, thereby illuminating the cavity 24 and initiates with the control 40 an automated hole inspection cycle. The control 40 first commands the machine 36 to move the camera 38 to a location over the next hole to be inspected such that the camera centerline 42 is substantially colinear with the hole centerline 52. After the programmable motion controller 150 determines that the camera is in position, the computer 188 then, at 414, receives a picture from a frame grabber 189 that is connected to the camera 38. The computer 188 then creates, at 416, a histogram of light intensities within a region of interest within the picture.

As will be appreciated, the camera 38 has a field of view that collects light from a plurality of cooling holes; however, the inspection process requires that light be detected from individual cooling holes. Therefore, a region of interest within the field of view is identified for processing. Knowing the area or size of the cooling hole to be processed, the location of its centerline and the spacing between the cooling holes, a region of interest can be defined that is larger than the cooling hole being inspected but does not encompass adjacent cooling holes. Thus, at 418, the computer 188 generates a histogram of light intensity values within the region of interest and identifies and stores a maximum intensity value within the region of interest. It should be noted that the absolute value of light intensity in lumens is not necessary. Relative values of the detected intensity can be used, so that a maximum intensity value relative to the other intensity values in the histogram can be identified. Thus, the intensity values can simply be identified as a percentage of some scale, for example, the maximum value of the A/D converter used to receive the analog signal from the camera 38.

The computer 188 then determines, at 420, whether the stored maximum intensity value exceeds an intensity threshold value. As will be appreciated, even with an opaque covering over the machine 36, there is still some level of ambient light. Therefore, the stored maximum intensity value must exceed this intensity threshold value in order to associate the stored intensity value with light coming through one of the holes 22. If the computer 188 determines the stored intensity value is not greater than the intensity threshold value, error data is created and stored, at 422, for subsequent reporting. If the computer 188 determines that the stored intensity value is greater than the intensity threshold value, that data indicating the presence of a cooling hole 22 is also stored. Thereafter, at 424, the computer 188 whether the most recent cooling hole inspected is the last cooling hole to be inspected. If not, the computer 188 iterates through process steps 412–424 of the inspection cycle until the last cooling hole on the component has been inspected.

Upon completion of inspecting the last cooling hole, the computer 188 then proceeds to create, at 426, an inspection report that can be viewed and/or printed by the operator. The report can be tailored to a user's preferences and can be used to identify the component 20, the inspection results of all of the cooling holes inspected, the number of cooling holes that did and did not pass inspection, etc. At this point, another component 20 can be loaded on the inspection machine.

Figure 5:
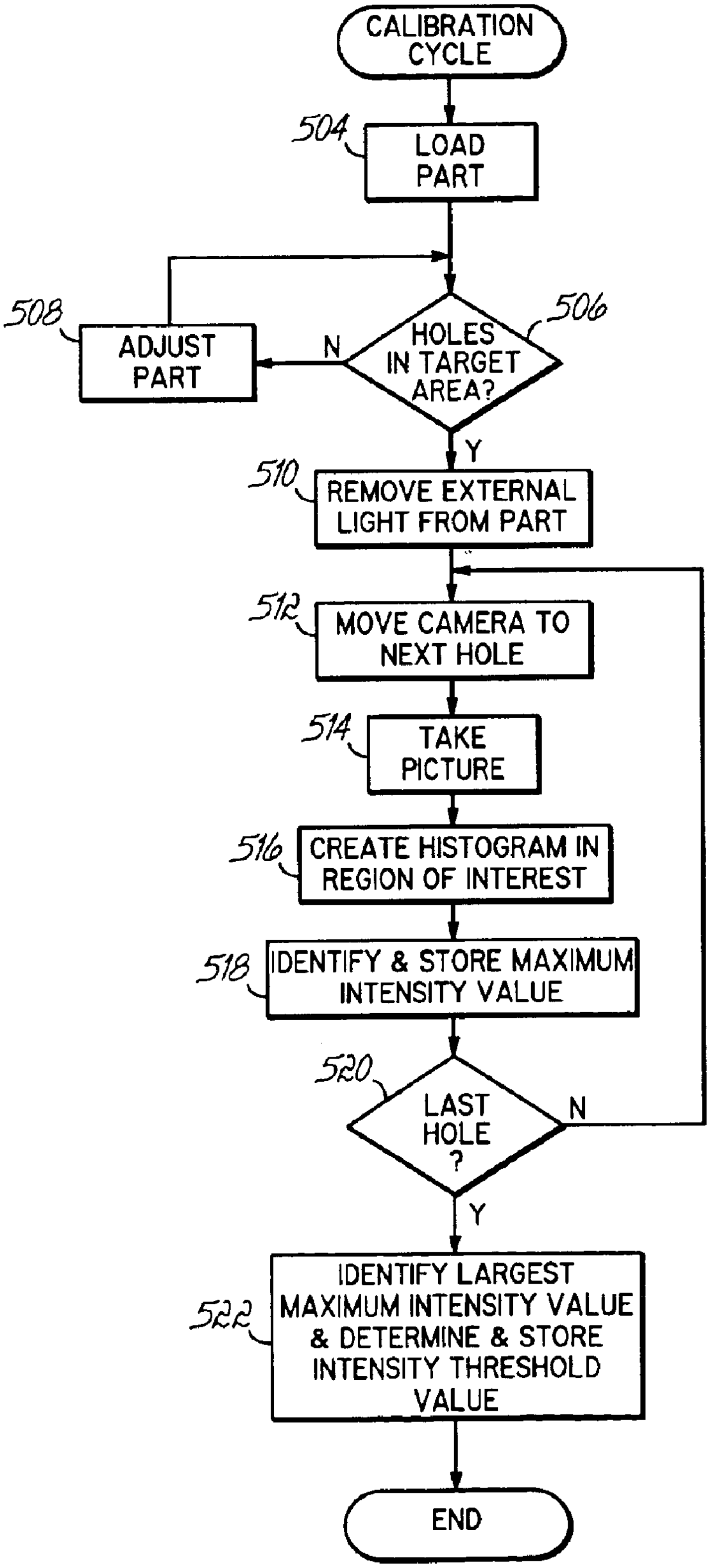
FIG. 5 is a flowchart of an inspection setup cycle for using the light inspection system of FIG. 1.

In executing the inspection cycle of FIG. 4, it is necessary to have available an intensity threshold value representing the maximum ambient light one would expect the camera to receive without the light source 50 being illuminated. In determining the intensity threshold value, a calibration cycle of FIG. 5 is executed. In essence, the intensity threshold value is determined by measuring the maximum light intensity value at each cooling hole location without the cavity being illuminated and identifying the maximum intensity value. Thus, the process of FIG. 5 is very similar to the process of FIG. 4. For example, process steps 504–510 are substantially identical to the previously described process steps 404–410.

After determining that all of the cooling holes are in the target area and external light is removed from the component 20, in process steps 512–518, a maximum intensity value of light in the region of interest over cooling hole is identified and stored in a manner that is substantially identical to the previously described process steps 412–418. The computer 188 repeats the process steps 512–518 for each of the cooling holes; and when it determines, at 520, that the maximum intensity value for the last cooling hole has been stored, the computer then determines, at 522, which of the stored maximum intensity values is the largest and uses the largest maximum intensity value to determine and store an intensity threshold value that is used during the inspection cycle of FIG. 4.

As will be appreciated, there are various methods for determining the intensity threshold value that is used in the inspection cycle of FIG. 4. For example, in one embodiment, the largest maximum intensity value identified, at 526 in FIG. 5, is used. In another embodiment, the largest maximum intensity value identified at 526 is increased by some percentage, for example, two percent, five percent, ten percent, etc.; and that increased value is used as the intensity threshold value.

In a still further embodiment, process steps 512–522 are iterated to determine a largest maximum intensity value with the cavity 24 not illuminated as described above. Thereafter, process steps 512–516 are repeated for all of the cooling holes with the cavity 24 illuminated by the light source 50. However, with the cavity 24 illuminated, the computer 188 identifies and stores a minimum intensity value of each of the holes and thereafter, identifies and stores a smallest of the minimum intensity values. Next, an average of the largest maximum intensity value and the smallest minimum intensity value is determined. That average intensity value is added to the maximum intensity value, and that sum is stored as the intensity threshold value. As an alternative to this embodiment, a number, for example, 10, identical components 20 are processed to determine the largest maximum intensity value and the smallest minimum intensity value.

A particular method chosen to determine the intensity threshold value will depend on the configuration of the component 20, the pattern of cooling holes 22, the configuration of cavity 24, the type of light source 50, the ability to remove external light from the component during the inspection process, user preference, etc.

The hole inspection apparatus of FIG. 2 is substantially automated, faster, more error-free and less expensive than known tactile and visual inspection methods. Thus, the inspection apparatus is especially useful for inspecting a presence and quality of a large number of complex cooling holes in gas turbine component.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. For example, while the hole inspection process described herein is directed to an application for inspecting cooling holes in a turbine component, as will be appreciated, the described hole inspection process can be used to inspect holes in other parts, for example, fuel injectors, spray nozzles, combustors, stator blades, etc. Further, in the described embodiment during the calibration cycle, all of the holes are used to establish an intensity threshold value. As will be appreciated, in alternative embodiments of the calibrating cycle, less than all of the holes, or only one hole, may be used to determine an intensity threshold value.

Therefore, the invention in its broadest aspects is not limited to the specific details shown and described. Consequently, departures may be made from the details described herein without departing from the spirit and scope of the claims which follow.

What is claimed is:

1. A hole inspection system for inspecting complex holes extending between an outer surface of a wall of a structure and an inner surface forming a cavity in the structure, each of the complex holes having an outer portion having a larger cross-sectional area adjacent the outer surface and a smaller cross-sectional area within the wall, and each of the complex holes having an inner portion extending between the smaller cross-sectional area and an inlet opening on the inner surface of the cavity, the hole inspection system comprising:

a light source emitting light over its length and adapted to be inserted in the cavity and provide light through the complex holes;

a multi-axes machine having a camera mounted thereon, the camera having a lens and being movable by the machine to inspection positions at which the lens is substantially centered over a respective complex hole; and a control connected to the multi-axes machine and the camera and being operable to cause the multi-axes machine to move the camera to successive inspection positions, the control processing substantially only light intensity values representing light shining through a complex hole associated with a respective inspection position.

2. The hole inspection system of claim 1 wherein the light source has an illuminated portion with a length substantially equal to a length of the cavity.

3. The hole inspection system of claim 1 wherein the light source comprises a fiber optic light source.

4. A method of inspecting a plurality of complex holes extending between an outer surface of a wall of a structure and an inner surface forming a cavity in the structure, each of the plurality of complex holes having an outer portion having a larger cross-sectional area adjacent the outer surface and a smaller cross-sectional area within the wall, and each of the plurality of complex holes having an inner portion extending between the smaller cross-sectional area and an inlet opening on the inner surface of the cavity, the method comprising:

illuminating the cavity with a light source emitting light over its length;

moving automatically a camera to an inspection position with respect to one of the plurality of complex holes at which the camera would receive light from the one of the plurality of complex holes if the one of the complex holes is properly formed;

determining automatically a maximum intensity value of the light received by the camera from the one of the plurality of complex holes;

comparing automatically the maximum intensity value to a threshold value;

creating automatically error data identifying the one of the plurality of complex holes in response to the maximum intensity value being less than the threshold value; and iterating automatically the steps of moving, determining, comparing and creating for each of the plurality of complex holes.

5. The method of claim 4 wherein at the inspection position a centerline of a lens of the camera is substantially collinear with a centerline of a respective complex hole.

6. A method of inspecting complex holes extending between an outer surface of a wall of a structure and an inner surface forming a cavity in the structure, each of the complex holes having an outer portion with a larger cross-sectional area adjacent the outer surface and a smaller cross-sectional area within the wall, and each of the complex holes having an inner portion extending between the smaller cross-sectional area and an inlet opening on the inner surface of the cavity, the method comprising:

illuminating the cavity with a light source emitting light over its length;

moving automatically a camera to an inspection position with respect to each of the complex holes at which the camera would receive light from a respective complex hole if the respective complex hole is properly formed;

determining automatically a maximum intensity value of the light received by the camera from each of the complex holes;

comparing automatically the maximum intensity value to a threshold value; and creating automatically error data identifying one of the complex holes in response to a respective maximum intensity value being less than the threshold value.

7. The method of claim 6 wherein determining automatically a maximum intensity value further comprises:

storing substantially only light intensity values representing light shining through a complex hole associated with the respective inspection position; and identifying the maximum intensity value as a largest of the light intensity values.

8. The method of claim 7 further comprising detecting light intensity values within a field of interest representing the light shining through the respective complex hole associated with the inspection position.

9. The method of claim 8 wherein the inspection position comprises a camera location where the larger cross-sectional area of the one of the complex holes is substantially centrally located in a the field of interest.

10. The method of claim 7 further comprising creating a histogram from the light intensity values in order to identify the maximum intensity value.

11. The method of claim 6 wherein the inspection position comprises a camera location where the larger cross-sectional area of the one of the complex holes is substantially centrally located in a field of view of the camera.

12. The method of claim 6 wherein the inspection position comprises a camera location where a centerline of a lens of the camera is substantially collinear with a centerline of the respective complex hole.

13. A method of calibrating a light inspection system for inspecting a plurality of complex holes extending between an outer surface of a wall of a structure and an inner surface forming a cavity in the structure, each of the plurality of complex holes having an outer portion having a larger cross-sectional area adjacent the outer surface and a smaller cross-sectional area within the wall, and each of the plurality of complex holes having an inner portion extending between the smaller cross-sectional area and an inlet opening on the inner surface of the cavity, the method comprising:

moving automatically a camera to an inspection position with respect to one of the plurality of complex holes at which the larger cross-sectional area of the one of the complex holes is substantially centrally located in a field of view of the camera;

determining automatically, with the cavity not being illuminated, a maximum intensity value of the light received by the camera; and determining a threshold intensity value larger than the maximum intensity value.

14. The method of claim 13 wherein determining automatically a maximum intensity value further comprises:

storing substantially only light intensity values representing light being substantially directly over the one of the plurality of complex holes; and identifying the maximum intensity value as a largest of the light intensity values.

15. The method of claim 14 further comprising prior to storing, detecting light intensity values within a field of interest representing the light being substantially directly over the one of the plurality of complex holes.

16. The method of claim 14 further comprising creating a histogram from the light intensity values in order to identify the maximum intensity value.

17. The method of claim 13 further comprising:

iterating automatically the steps of moving and determining automatically a maximum intensity value for each of the plurality of complex holes;

identifying a largest maximum intensity value; and determining the threshold intensity value greater than the largest maximum intensity value.

18. A method of calibrating a light inspection system for inspecting complex holes extending between an outer surface of a wall of a structure and an inner surface forming a cavity in the structure, each of the complex holes having an outer portion with a larger cross-sectional area adjacent the outer surface and a smaller cross-sectional area within the wall, and each of the complex holes having an inner portion extending between the smaller cross-sectional area and an inlet opening on the inner surface of the cavity, the method comprising:

moving automatically a camera to an inspection position with respect to one of the complex holes at which the larger cross-sectional area of the one of the complex holes is aligned with a region of interest within a field of view of the camera;

determining automatically, with the cavity not being illuminated, a maximum intensity value of light within the region of interest from the one of the complex holes; and determining automatically a threshold value greater than the maximum intensity value.

19. The method of claim 17 wherein determining automatically a maximum intensity value further comprises:

storing substantially only light intensity values received from the camera within a field of interest;

creating a histogram from the light intensity values in order to identify the maximum intensity value; and identifying the maximum intensity value as a largest of the light intensity values.

20. The method of claim 19 further comprising iterating the steps of moving and determining automatically a maximum intensity value for all of the complex holes.

21. A method of calibrating a light inspection system for inspecting complex holes extending between an outer surface of a wall of a structure and an inner surface forming a cavity in the structure, each of the complex holes having an outer portion with a larger cross-sectional area adjacent the outer surface and a smaller cross-sectional area within the wall, and each of the complex holes having an inner portion extending between the smaller cross-sectional area and an inlet opening on the inner surface of the cavity, the method comprising:

moving automatically a camera to inspection positions with respect to a plurality of the complex holes at which the larger cross-sectional area of a respective complex hole is aligned with a region of interest within a field of view of the camera;

determining automatically, with the cavity not being illuminated, a maximum intensity value of the light within the field of interest for each of the plurality of the complex holes;

illuminating the cavity with a light source;

moving automatically a camera to the inspection positions with respect to the plurality of the complex holes;

determining automatically a minimum intensity value of the light within the field of interest for each of the plurality of the complex holes; and determining automatically a threshold value greater than the maximum intensity value.

22. The method of claim 21 wherein determining automatically a threshold value further comprises:

determining an average value of the maximum intensity value and the minimum intensity value; and summing the average value and the maximum intensity value to provide the threshold value.

* * * * *

UNITED STATES PATENT AND TRADEMARK OFFICE

CERTIFICATE OF CORRECTION

PATENT NO. : 6,963,396 B2 
DATED : November 8, 2005
INVENTOR(S) : Dwight Evans Kimberlin It is certified that error appears in the above-identified patent and that said Letters Patent is hereby corrected as shown below:

Column 1,
Lines 20-21, "damage and, to extend" should read -- damage to, and extend --.
Line 24, "small have" should read -- small and have --.
Line 58, "holes in gas" should read -- holes in a gas --.

Column 5,
Line 8, "length 52 be able" should read -- length 52 may be able --.
Line 37, "cable, The" should read -- cable. The --.
Lines 38 and 41, "heatshink" should read -- heatshrink --.

Column 6,
Lines 50-51, "computer 188 whether" should read -- computer 188 determines whether --.

Column 7,
Line 62, "holes in gas" should read -- holes in a gas --.
Line 66, "applicants" should read -- applicant --.

Column 9,
Line 49, "located in a field" should read -- located in the field --.

Column 10,
Line 22, "further comprising prior" should read -- further comprising, prior --.

Signed and Sealed this

Twenty-eighth Day of March, 2006

JON W. DUDAS
*Director of the United States Patent and Trademark Office*